(12) United States Patent
Wakamatsu et al.

(10) Patent No.: US 6,737,559 B2
(45) Date of Patent: May 18, 2004

(54) SEE-THROUGH MEDAKA

(75) Inventors: Yuko Wakamatsu, c/o Bioscience Center, Nagoya University, Furo-cho, Chikusa-ku, Nagoya-shi, Aichi 464-8601 (JP); Kenjiro Ozato, c/o Bioscience Center, Nagoya University, Furo-cho, Chikuda-ku, Nagoya-shi, Aichi 464-8601 (JP); Minoru Tanaka, Hokkaido (JP); Masato Kinoshita, Kyoto (JP)

(73) Assignees: Yuko Wakamatsu (JP); Kenjiro Ozato (JP)

( * ) Notice: Subject to any disclaimer, the term of this patent is extended or adjusted under 35 U.S.C. 154(b) by 0 days.

(21) Appl. No.: 09/814,047

(22) Filed: Mar. 22, 2001

(65) Prior Publication Data
US 2002/0112252 A1 Aug. 15, 2002

(30) Foreign Application Priority Data

Jun. 8, 2000 (JP) ........................................ 2000-172375

(51) Int. Cl.[7] ...................... A01K 67/027; C12N 15/00
(52) U.S. Cl. ........................................... 800/20; 800/22
(58) Field of Search ........................................... 800/20

(56) References Cited

FOREIGN PATENT DOCUMENTS

| WO | WO 98/28971 | 7/1998 |
| WO | WO 98/56902 | 12/1998 |

OTHER PUBLICATIONS

Linney et al., Transgene expression in zebrafish: A comparison of retroviral–vector and DNA–injection approaches, 1999, Developmental Biology, vol. 213, pp. 207–216.*
Ozato et al. Developmental genetics of medaka, 1994, Developmental Growth & Differentiation, vol. 36, pp. 437–443.*
Tanaka et al., establishment of medaka (Oryzias latipes) transgenic lines with the expression of green fluorescent . . . , 2001, PNAS, vol. 98, pp. 2544–2549.*
Shimada A. et al.: "Establishment of a Multiple Recessive Tester Stock in the Fish Oryzias–latipes" Zoological Science, vol. 5, No. 4, pp. 897–900, (1988).
Wakamatsu Y. et al.: "The see–through medaka: a fish model that is transparent throughout life" Proceedings of The National Academy of Sciences of USA, vol. 98, No. 18, pp. 10046–10050, (Aug. 28, 2001).
Hamada, K. et al.: "Usefulness of the medaka beta–actin promoter investigated using a mutant GFP reporter gene in transgenic medaka (Oryzias–latipes)", Mol Mar Biol Biotechnol, vol. 7, (3), pp. 173–180 (Sep. 1998) (abstract).
Koga, A. et al.: Oculocutaneous albinism in the i6 mutant of the medaka fish is associated with a deletion in the tyrosinase gene. Pigment Cell Res, vol. 12, (4), pp. 252–258, (Aug. 1999) (abstract).

Inagaki et al.: "Expression of the tyrosinase–encoding gene in a colorless melanophore mutant of the medaka fish, Oryzias–latipes", Gene, 150, (2), pp. 319–324, (1994) (abstract).
Hatakeyama, S. et al., 2001, "Effects of 17β–estradiol ($E_2$) on sex–reversal of male Medaka (*Oryzias latipes*), FLF–strain, and reproductive potential of the sex–reversed or not reversed individuals," *Jpn. J. Environ. Toxicol.*, 4(2): 99–111.
Higashijima, S. et al., 1997, "High–Frequency Generation of Transgenic Zebrafish Which Reliably Express GFP in Whole Muscles or the Whole Body by Using Promoters of Zebrafish Origin," *Developmental Biology*, 192: 289–299.
Higashijima, S. et al., 2000, "Visualization of Cranial Motor Neurons in Live Transgenic Zebrafish Expressing Green Fluorescent Protein Under the Control of the *Islet–1* Promoter/Enhancer," *The Journal of Neuroscience*, 20(1): 206–218.
Kinoshita, M. et al., 2000, "Activity of the medaka translation elongation factor 1α–A promoter examined using the GFP gene as a reporter," *Develop. Growth Differ.*, 42: 469–478.
Kusakabe, R. et al., 1999, "In vivo analysis of two striated muscle actin promoters reveals combinations of multiple regulatory modules required for skeletal and cardiac muslce–specific gene expression," *Int. J. Dev. Biol.*, 43: 541–554.
Long, Q. et al., 1997, "*GATA–1* expression pattern can be recapitulated in living transgenic zebrafish using GFP reporter gene," *Development*, 124: 4105–4111.
Niwa, K. et al., 2000, "Expression of GFP in Nuclear Transplants Generated by Transplantation of Embryonic Cell Nuclei from GFP–Transgenic Fish into Nonenucleated Eggs of Medaka, *Oryzias latipes*," *Cloning*, 2(1): 23–34.
Shimada, A. et al., 1988, "Establishment of a Multiple Recessive Tester Stock in the Fish *Oryzias latipes*, " *Zoological Science*, 5: 897–900.

(List continued on next page.)

*Primary Examiner*—Anne-Marie Falk
*Assistant Examiner*—Celine Qian
(74) *Attorney, Agent, or Firm*—Finnegan, Henderson, Farabow, Garrett, & Dunner, L.L.P.

(57) ABSTRACT

This invention relates to a see-through medaka deficient in iridophores, melanophores, xanthophores and leucophores; a see-through medaka deficient in iridophores, melanophores and xanthophores, and whose sex can be identified by the presence or absence of leucophores and/or a DNA marker; and a see-through medaka wherein a specific organ is allowed to produce luminescence by introducing a hybrid gene being a fusion of a promoter of a gene expressing specifically in that organ and a coding region of a gene encoding a fluorescent protein.

30 Claims, 5 Drawing Sheets

OTHER PUBLICATIONS

Takana, M. et al., 1999, "Inbred Medaka Transgenics Expressing GFP in Germ Cells," Abstract from The 22$^{nd}$ Annual Meeting of the Molecular Biology Society of Japan, Dec. 7 to 10, 1999, published in Reproductive Biol., Aug. 1999, p. 458 (including translation).

Tomita, H., 1975, "21. Mutant Genes in the Medaka," from *Medaka (KILLIFISH): Biology and Strains*, T. Yamamoto ed., Keigaku Publishing Company, Tokyo, Japan, pp. 251–272.

Tomita, H., 1992, "The lists of the mutants and strains of the medaka, common gambusia, silver crucian carp, goldfish, and golden venus fish maintained in the Laboratory of Freshwater Fish Stocks, Nagoya University," *The Fish Biology Journal Medaka*, 4: 45–47.

Wakamatsu, Y. et al., 2001, "Fertile and diploid nuclear transplants derived from embryonic cells of a small laboratory fish, medaka (*Oryzias latipes*)," *PNAS*, 98(3): 1071–1076.

Wakamatsu, Y. et al., 2001, "The see–through medaka: A fish model that is transparent throughout life," *PNAS*, 98(18): 10046–10050.

* cited by examiner

Parental strains of ST-II a: Iridophore deficient mutant gu b: Albino mutant i-3 c: Leucophore deficient mutant lf

Results of electrophoresis on DNA (presence of DNA marker SL1) of STII-YI see-through medaka a : Female see-through medaka of STII-YI strain Lane: 1 2 3 4 5 6 7 8 9 10 11 12 b : Male see-through medaka of STII-YI strain

SEQUENCE LISTING

```
<160> NUMBER OF SEQ ID NOS: 8

<210> SEQ ID NO 1
<211> LENGTH: 25
<212> TYPE: DNA
<213> ORGANISM: Oryzias latipes
<220> FEATURE:
<223> OTHER INFORMATION: Forward primer pHO5.5-F.

<400> SEQUENCE: 1
cctgcaatgg gaaattattc tgctc                                        25

<210> SEQ ID NO 2
<211> LENGTH: 28
<212> TYPE: DNA
<213> ORGANISM: Oryzias latipes
<220> FEATURE:
<223> OTHER INFORMATION: Reverse primer pHO5.5-RV.
```

<400> SEQUENCE: 2
cttttgtgtc tttggttatg aaacgatg                                    28

<210> SEQ ID NO 3
<211> LENGTH: 19
<212> TYPE: DNA
<213> ORGANISM: Unknown
<220> FEATURE:
<221> NAME/KEY: modified_base
<222> LOCATION: (6), (12), (18)
<223> OTHER INFORMATION: represents a, g, t, or c
<223> OTHER INFORMATION: Common sequence found in animals. The sequence
      is used herein as a forward primer to amplify the short fragment of
      vasa cDNA.

<400> SEQUENCE: 3
atggcntgyg cncaracng                                              19

<210> SEQ ID NO 4
<211> LENGTH: 18
<212> TYPE: DNA
<213> ORGANISM: Unknown
<220> FEATURE:
<221> NAME/KEY: modified_base
<222> LOCATION: (4)
<223> OTHER INFORMATION: represents a, g, t, or c
<223> OTHER INFORMATION: Common sequence found in animals. The sequence
      is used herein as a reverse primer used to amplify the short
      fragment of vasa cDNA.

<400> SEQUENCE: 4
raancccatr tcyaacat                                               18

<210> SEQ ID NO 5
<211> LENGTH: 20
<212> TYPE: DNA
<213> ORGANISM: Oryzias latipes
<220> FEATURE:
<223> OTHER INFORMATION: Primer T7 used to amplify the 3'region of vasa
      gene.

<400> SEQUENCE: 5
taatacgact cactataggg                                             20

<210> SEQ ID NO 6
<211> LENGTH: 23
<212> TYPE: DNA
<213> ORGANISM: Oryzias latipes
<220> FEATURE:
<223> OTHER INFORMATION: Other information: Primer VI-8 used to amplify
      the 3'region of vasa gene.

<400> SEQUENCE: 6
aggaggtgcc gtcatggctg gag                                         23

<210> SEQ ID NO 7
<211> LENGTH: 30
<212> TYPE: DNA
<213> ORGANISM: Oryzias latipes
<220> FEATURE:
<223> OTHER INFORMATION: Other information: Primer VP1M used to amplify
      5.1 kb genomic fragment comprising the promotor region of vasa
      gene.

<400> SEQUENCE: 7
cctcccagtc gtccatatga atcgtctgat                                  30

```
<210> SEQ ID NO 8
<211> LENGTH: 37
<212> TYPE: DNA
<213> ORGANISM: Oryzias latipes
<220> FEATURE:
<223> OTHER INFORMATION: Other information: Primer VP3 used to amplify
      5.1 kb genomic fragment comprising the promotor region of vasa
      gene.

<400> SEQUENCE: 8
agaggatcca atagaatgag taatggttct ctatttc                              37
```

SEE-THROUGH MEDAKA

FIELD OF THE INVENTION

The present invention relates to the development of a novel see-through medaka, a see-through medaka whose sex can be identified, and a see-through medaka in which specific organs produce luminescence.

BACKGROUND OF THE INVENTION

Fifteen species belonging to genus Oryzias (Medaka) are known and are distributed in the Asian area from India to Japan. A species having its habitat in Japan is *Oryzias latipes*, which is also distributed in parts of China and Korea. With the exception of the Hokkaido area, it is distributed throughout Japan, and propagates during May to August in the natural world.

Common wild medaka has a dark body color and this is due to four types of pigment cells in the skin of medaka: iridophore, melanophore, xanthophore and leucophore. The iridophore is a silver pigment cell containing guanine granules. The iridophore is distributed prevalently in opercula, eyeballs, body wall and epidermis. In fish, it is distributed mainly in the ventral. The melanophore contains melanin granules and is involved in the dark body color of medaka. The xanthophore has pigment granules containing carotenoids and pteridines, and is involved in yellowish orange body color of medaka. The leucophore contains white granules compacted with pterine and uric acid, and is involved in white body color of medaka. Apart from the wild type which has a dark body color, there are known various mutants in relation to body color and morphogenesis. Among them, "himedaka" which has a yellowish orange body color is produced on a large scale as an aquarium fish and feed for large aquarium fishes.

Medaka is widely used as a simple and useful experimental animal due to a small body size of 2–4 cm, a short term for sexual maturation of 2 months, the fact that due to their wide distribution, the wild type population and closely-related species are easily obtainable and because its genome is ⅕ the size of mammals', and sex determination is by X and Y chromosomes as in humans. The embryo of medaka is especially useful, since it is highly transparent with an easily observable internal structure. After hatching, however, since the epidermis and the peritoneum are covered with pigment cells, only the backbone can be seen through the body and the observation of the internal structure of the body from the outside becomes difficult.

Attempts have made recently at visualization of in vivo changes occuring in the internal structure by introducing a specific gene in Xenopus (amphibian) [Louie, A. Y. et al., In vivo visualization of gene expression using magnetic resonance imaging. Nature Biotechnology, 18, 321–325 (2000)]; and mice [Service, R. F., Scanners get a fix on lab animals. Science, 286, 2261–2263 (1999)], and tracing protein, a product of this gene, with MRI (magnetic resonance imaging), CT scanner (computed tomography scanner) or PET (position emission topography). These methods can, however, only provide insufficient images in spite of their requiring large and expensive equipment.

Further, there have been attempts at the lifelong tracing of the dynamics of certain organs by providing these organs with luminescence by means of GFP. Such studies are being performed with mouse tumor tissue, but observation can only be made at a maximum subcutaneous depth of 2 mm. [Yang, M. et al., Whole-body optical imaging of green fluorescent protein-expressing tumors and metastasis. PNAS, 97, 1206–1211 (2000)]. Expression of GFP fluorescence in transgenic medaka by introduction of a GFP gene fused with a medaka gene promoter into fertilized eggs, is known. [Hamada, K. et al., Usefulness of the medaka β-actin promoter investigated using a mutant GFP reporter gene in transgenic medaka (*Oryzias latipes*). Mol. Marine Biol. Biotech., 7, 173–180 (1998)]. Tanaka, Minoru and Kinoshita, Masato, and Nagahama, Yoshitaka produced a transgenic medaka with green fluorescence in only germ cells as a result of introducing vasa-GFP gene into fertilized eggs of himedaka [in The 22nd Annual Meeting of the Molecular Biology Society of Japan, Program, Abstract, pp. 458 (1999), Tanaka, Minoru, Kinoshita, Masato and Nagahana, Yoshitaka, "Inbred medaka transgenics expressing GFP in germ cells"]. However, even in this transgenic medaka, fluorescence can only be observed up to the term immediately after hatching, and thereafter the body is covered with pigment cells and the observation becomes impossible.

For the above reasons, it is desirable that there be developed an experimental animal in which life-long observation of the internal structure of the body from the outside is possible. However, no such the experimental animal is known at present in vertebrates.

SUMMARY OF THE INVENTION

An object of the present invention is to provide a see-through medaka, in which the internal body structure thereof can be observed from the outside not only in the embryonic stage but also in the post-hatching stage. Another object of the present invention is to provide a see-through medaka, whose sex can be indentified. A further object of the present invention is to provide a see-through medaka, in which specific organs produce luminescence.

The inventors have studied extensively to solve the above problems, and have succeeded as a result of selective mating among mutant medaka, deficient in one or more types of pigment cells among the four types of pigment cells constituting dark color of medaka, to produce a medaka in which the internal body structure thereof can be observed from the outside not only in the embryonic stage but also in the post-hatching stage, thereby completed the present invention.

(i) The present invention relates to a see-through medaka wherein said medaka is deficient in iridophores, melanophores, xanthophores and leucophores.

(ii) Further, the present invention relates to the see-through medaka of (i) above wherein said medaka is produced by means of repeated selective mating between iridophore deficient mutant medaka strain gu, albino mutant medaka strain i-3 and leucophore deficient mutant medaka strain lf.

(iii) Further, the present invention relates to a see-through medaka wherein said medaka is produced by means of further selective mating between the see-through medaka in the (ii) above and iridophore deficient mutant medaka strain il-1.

(iv) The present invention relates further to a see-through medaka wherein said medaka is deficient in iridophores, melanophores and xanthophores, and wherein the sex of said medaka can be identified by the presence or absence of leucophores and/or a DNA marker.

(v) The present invention relates to the see-through medaka of (iv) above wherein said medaka is produced by means of repeated selective mating between iridophore deficient mutant medaka strain gu, albino mutant medaka strain i-3, leucophore deficient mutant medaka strain lf and medaka FLF strain which is deficient in leucophore in the female.

(vi) The present invention relates to a see-through medaka wherein said medaka is produced by means of further selective mating between the see-through medaka of (iii) above and the see-through medaka of (v) above.

(vii) Further, the present invention relates to the see-through medaka according to any one of (i) to (vi) above wherein a specific organ is allowed to produce luminescence by introducing a hybrid gene being a fusion of a promoter of a gene which expresses specifically in said organ with a coding region of a gene encoding a fluorescent protein.

(viii) Further, the present invention relates to the see-through medaka according to (vii) above wherein said gene encoding the fluorescent protein is a gene encoding a green fluorescent protein.

(ix) Further the present invention relates to the see-through medaka according to (vii) or (viii) above wherein said organ is a gonadal organ.

The present invention will be explained hereinbelow in detail,

BRIEF DESCRIPTION OF DRAWINGS

FIG. 3: A pattern of electrophoresis showing a result of PCR analysis of DNA marker SL1 in STII-YI strain.

Figure 1:
FIGS. 1A–C: Photographs of body color mutant medaka, wherein a. is iridophore deficient mutant strain gu; b. is albino mutant strain i-3; and c. is leucophore deficient mutant strain lf.
Figure 1:
Figure 1:

This specification includes part or all of the contents as disclosed in the specification and/or drawings of Japanese Application No. 2000/172375, which is a priority document of the present application.

DESCRIPTION OF THE PREFERRED EMBODIMENTS (1) The See-through medaka of the present invention is characterized in that it is deficient in iridophores, melanophores, xanthophores and leucophores.

"See-through" used in the present description means that in medaka not only in the embryonic stage but also in the post-hatching stage, internal body structures such as brain, spinal cord, blood vessels, gill, heart, liver, kidneys, spleen, intestine and air bladder, can be observed macroscopically from the outside.

"Deficient" means that in medaka, the above four types of pigment cells (iridophore, melanophore, xanthophore and leucophore) are completely absent or, if present, are present in very small numbers, or if the above cells are present, no intracellular pigment is present or only trace pigment is present, and the contribution of these pigment cells to the body color of medaka can not be observed macroscopically.

Medaka of the present invention can be produced, for example, by repeated selective mating of body color mutant medaka with each other, which are deficient in one or more pigments cells of the 4 types of pigment cells (iridophore, melanophore, xanthophore and leucophore), but the production of the present invention is not limited to this method.

"Selective mating" means selecting the individuals of desired phenotype or genotype from one generation to be mated thereby producing the next generation.

Examples of body color mutant medaka used for the selective mating include but are not limited to iridophore deficient mutant medaka (such as gu strain or il-1 strain), albino mutant medaka (such as i-3 strain) or leucophore deficient mutant medaka (such as lf strain). These medaka strains are maintained in the Bioscience Center, Nagoya Univ. and can be furnished therefrom.

Concretely, the see-through medaka of the present invention can be produced by means of repeated selective mating with iridophore deficient mutant medaka strain gu, albino mutant medaka strain i-3 and leucophore deficient mutant medaka strain lf (the see-through medaka of (ii) above).

Further, a see-through medaka produced by additional selective mating between one or more types of strains in order to increase transparency, is included in the see-through medaka of the present invention. Concretely, a see-through medaka is produced by means of further selective mating with the see-through medaka in the (ii) above and iridophore deficient mutant medaka strain il-1 (the see-through medaka of the (iii) above).

The see-through medaka of the present invention can be obtained by furnishing from the Bioscience Center, Nagoya Univ. except whereas produced by the above method.

(2) Further, the see-through medaka of the present invention is deficient in iridophores, melanophores and xanthophores, and the sex thereof can be identified by the presence or absence of leucophores and/or a DNA marker.

"Sex identification by the presence or absence of leucophores" refers to identification as to whether a subject is male or female by microscopic observation of the presence or absence of leucophores in the period after the two-day-old embryo stage of the above see-through medaka.

"DNA marker" used in the present specification means DNA markers that are specific to genetic sex. "Sex identification by DNA markers" means that identification of whether a subject is male or female is performed by detecting DNA markers as a result of PCR on DNA of the individual medaka.

The see-through medaka of the present invention for which sex identification is possible can be produced by, for example, repeated selective mating between the see-through medaka of the present invention described in (ii) above and a strain, in which sex difference is apparent in respect of only the existence of leucophore, and/or a strain bearing a DNA marker, but this production is not limited hereto.

The strain, in which sex difference is apparent in respect of only the existence of leucophores, and the strain bearing a DNA marker can be different strains or the same strain. An example of a strain, in which sex difference is apparent in respect of only the existence of leucophores, is, for example, Qurt [Wada, H. et al., Sex-linked inheritance of the lf locus in the medaka fish (*Oryzias latipes*). Zool. Sci. 15:123–126 (1998), obtainable by furnishing from Dept. of Integrated Biosciences, Graduate School of Frontier Sciences, University of Tokyo]. An example of where these are the same strain is FLF (female leucophore free) strain, only the male of which has leucophores and a DNA marker [SLl (Matsuda. M. et al., Isolation of a sex chromosome-specific DNA sequence in the medaka, *Oryzias latipes*. Genes Genet. Syst. 72, 263–268 (1997))]; which can be obtained by furnishing from the Bioscience Center, Nagoya Univ. These are, however, are not limited to these examples. Also, a DNA marker per se is not limited to the above SLl, and any DNA marker known to a person skilled in the art can be used.

Concretely, the see-through medaka, for which sex identification is possible, of the present invention is produced by repeated selective mating between the see-through medaka of the present invention of (ii) above and the above medaka of FLF strain (the see-through medaka of (v) above).

Further, a see-through medaka with a highly increased transparency level obtained by selective mating between one or more strains is also included in the see-through medaka of the present invention for which sex identification is possible. Concretely, it can be produced by means of further selective mating between the see-through medaka of the (iii) above and the see-through medaka of the (v) above (the see-through medaka (vi) above).

Apart from by the above method of production, the see-through medaka for which sex identification is possible, can be obtained from the Bioscience Center, Nagoya Univ., where said medaka is maintained.

(3) Further, the see-through medaka of the present invention is characterized by the production of a luminescence in a specific organ thereof by introducing a hybrid gene being a fusion of a promoter of a gene that expresses organ-specifically and the coding region of the gene encoding a fluorescent protein, into the see-through medaka of the present invention of any one of (i) to (vi) above.

Examples of specific organs with luminescence include, but are not limited to gonadal tissues (germ cells), brain, nerves, liver and muscles, and can be selected depending on the purpose of an experiment.

As a promoter of a gene that expresses organ-specifically, any promoter can be selected depending on the organ which is to produce luminescence. For example, a vasa gene promoter specific to gonadal tissues (germ cells) can be used.

Examples of fluorescent protein gene are not limited to and are, for example, green fluorescent protein (hereinafter designated simply as "GFP") gene of *Aequorea victoria*, blue fluorescent protein (BFP) gene and yellow fluorescent protein (YFP) gene. These fluorescent protein genes are available from CLON TECH Inc. (1020 East Meadow Circle, Palo Alto, Calif., USA).

The see-through medaka of the present invention characterized by production of luminescence in a specific organ, can be produced, for example, by preparing transgenic medaka, to which is introduced a hybrid gene being a fusion of a promoter of gene specifically expressing in the organ that is to have luminescence and the coding region of the fluorescent protein gene; and repeating selective mating of said transgenic medaka with one or more body color mutant medaka strains.

The preparation of the hybrid gene produced by fusing the above promoter of a gene specifically expressing in an organ and the above coding region of a fluorescent protein gene, and the production of the transgenic medaka, to which the said hybrid gene is introduced, can be performed by any method known to a person skilled in the art, for example, a method described in the examples of the present invention.

An example of the above transgenic medaka is the vasa-GFP strain produced by introducing a hybrid gene, which is produced by fusing the promoter of the vasa gene which specifically expresses in germ cells (i.e. specific to gonadal tissue) with the coding region of GFP gene (Tanaka, Minoru et al., The 22nd Annual Meeting of the Molecular Biology Society of Japan, Program, Abstract, aforementioned), but the above transgenic medaka is not limited to this example.

Examples of a body color mutant medaka strain to be mated with the above transgenic medaka include, but are not limited to, a medaka strain known to a person skilled in the art, the see-through medaka strain of any one of (i) to (vi) above, and a new strain produced by crossing-over of sex chromosomes in the production of the see-through medaka (i) to (vi) above.

Concretely, the see-through medaka of the present invention emitting luminescence in a specific organ can be produced by repeated selective mating with the medaka of vasa-GFP strain, the see-through medaka of (ii) above and the see-through medaka of (v) above (for which sex identification is possible) (the see-through medaka of (ix) above). Further examples of the preferable see-through medaka of the present invention producing luminescence in a specific organ are the see-through medaka ("STII-YII-vasa-GFP" in the examples) produced by repeated selective mating between the female see-through medaka of (ix) above and the leucophore deficient (lf) male see-through medaka ("STII-YI-vasa-GFP (lf) in the examples) generated by the crossing-over of sex chromosomes in the see-through medaka of (ix) above; the see-through medaka ("STIII-YI-vasa-GFP" in the examples) produced by repeated selective mating between the see-through medaka of (iii) above and the see-through medaka of (ix) above; and the see-through medaka ("STIII-YII-vasa-GFP" in the examples) produced by repeated selective mating between the female see-through medaka of the STIII-YI-vasa-GFP strain and the leucophore deficient (lf) male see-through medaka ("STIII-YI-vasa-GFP (lf) in the examples) generated by the crossing-over of sex chromosomes in the see-through medaka of said strain.

The see-through medaka producing luminescence in a specific organ can also be produced by direct introduction of the above hybrid gene into the see-through medaka of (i)-(vi) above.

Direct introduction of the hybrid gene can be performed by methods known to a person skilled in the art, for example a method of microinjection of a gene into the cytoplasm of the one-cell-stage embryo.

The see-through medaka of the present invention which produces luminescence in a specific organ can be obtained, apart from the methods described above, from the Bio-science Center, Nagoya Univ., where said medaka is maintained.

EXAMPLES

The present invention will be explained in detail by illustration with the following examples, but these examples are only illustrative and are not intended to limit the scope of the present invention.

Example 1
Production of the See-Through Medaka (1) Production of STII Strain

The see-through medaka of the present invention was produced by using three strains of body color mutant (gu, i-3 and lf) as mating parents, selected from 120 mutant strains consisting of mainly spontaneous mutants collected by Tomita, Hideo since the early 1960's and stored in Nagoya University. These three strains are deficiet in one or more types of pigment cells among four types consituting body color of each medaka. Specific properties of each strain are shown as follows and in Table 1.

(Specific Properties of Each Strain)

gu: Iridophore Deficient Mutant (FIG. 1a)

The iridophore is a silver colored pigment cell, which is prevalent in the ventral skin of fish. Ventral white glistening is due to existence of this cell. In the gu mutant, accumulation of guanine is small in iridophores. Especially, a small amount of accumulation is observed in the peritoneum of adult fishes. It was found among medaka collected by Tomita, Hideo at Nagashima-Cho, Mie-Pref. in 1978.

i-3: Albino Mutant (FIG. 1b)

This mutant is deficient in melanotic melanin pigment, has the poor accumulation of yellow pigment and has a large number of leucophores, and as a result, the skin is white. Since it has no melanin in its retina, its eyes appear red. No melanin is observed in the peritoneum. This mutant was found among medaka collected by Tomita, Hideo in Tottori-city in 1976.

lf: Leucophore Deficient Mutant (FIG. 1c)

The leucophore is a white cell and is involved in changes of body color together with melanophore. This strain has no leucophore. It was collected by Tomita. Hideo in Toyokawa-city in 1971.

TABLE 1

Parental strains for mating

| Strain | Specific Features | Geno-type | Origin | Place of Deposit | Furnishing |
|---|---|---|---|---|---|
| gu | Less precipitation of guanine in peritoneum, skin and eyes | gu/gu | Nagashima-Cho, Mie-Pref. 1978 | Bioscience Center, Nagoya Univ. | Yes |
| i-3 | Albino | i-3/i-3 | Tottori-City, 1976 | Bioscience Center, Nagoya Univ. | " |
| lf | Deficient in leucophore | $X^{lf}/X(Y)^{lf}$ | Toyokawa-City, 1971 | Bioscience Center, Nagoya Univ. | " |

Using the above three strains, selective matings were repeated in order to obtain medaka having all of the specific properties of each of the parental strain as shown in Table 2 below.

TABLE 2

Mating data

| Mating No. | Generation of Parents ♀ | Generation of Parents ♂ | Descendant Generation Generation | Descendant Generation Genotype | Descendant Generation Phenotype |
|---|---|---|---|---|---|
| 1 | gu (i-3) | i-3 (gu) | $F_1$ | gu/+, i-3/+ | $+^{gu}, +^{i-3}$ |
| 2 | $F_1$ | $F_1$ | $F_2$ | gu/gu, i-3/i-3 (1/16 of $F_2$)* | gu, i-3 |
| 3 | $F_2$ | lf | $F_3$ | gu/+, i-3/+, $X^+/X(Y)^{lf}$ | $+^{gu}, +^{i-3}, +^{lf}$ |
| 4 | $F_3$ | $F_3$ | $F_4$ | gu/gu, i-3/i-3, $X^{lf}/Y^{lf}$ (1/64 of $F_4$, all ♂) | gu, i-3, lf (♂) |
| 5 | $F_3$ | $F_4$ | $F_5$ | gu/gu, i-3/i-3, $X^{lf}/X(Y)^{lf}$ (1/8 of $F_5$) | gu, i-3, lf |
| 6 | $F_5$ | $F_5$ | $F_6$ | gu/gu, i-3/i-3, $X^{lf}/X(Y)^{lf}$ (all individuals) | gu, i-3, lf |

(Results)

In the $F_6$ generation, a medaka having all specific properties of the parental strains, i.e. a medaka deficient in iridophores, melanophores, xanthophores and leucophores (genotype: gu/gu, i-3/i-3, $X^{lf}/X(Y)^{lf}$, phenotype: gu, i-3, lf) was obtained.

Figure 2A:
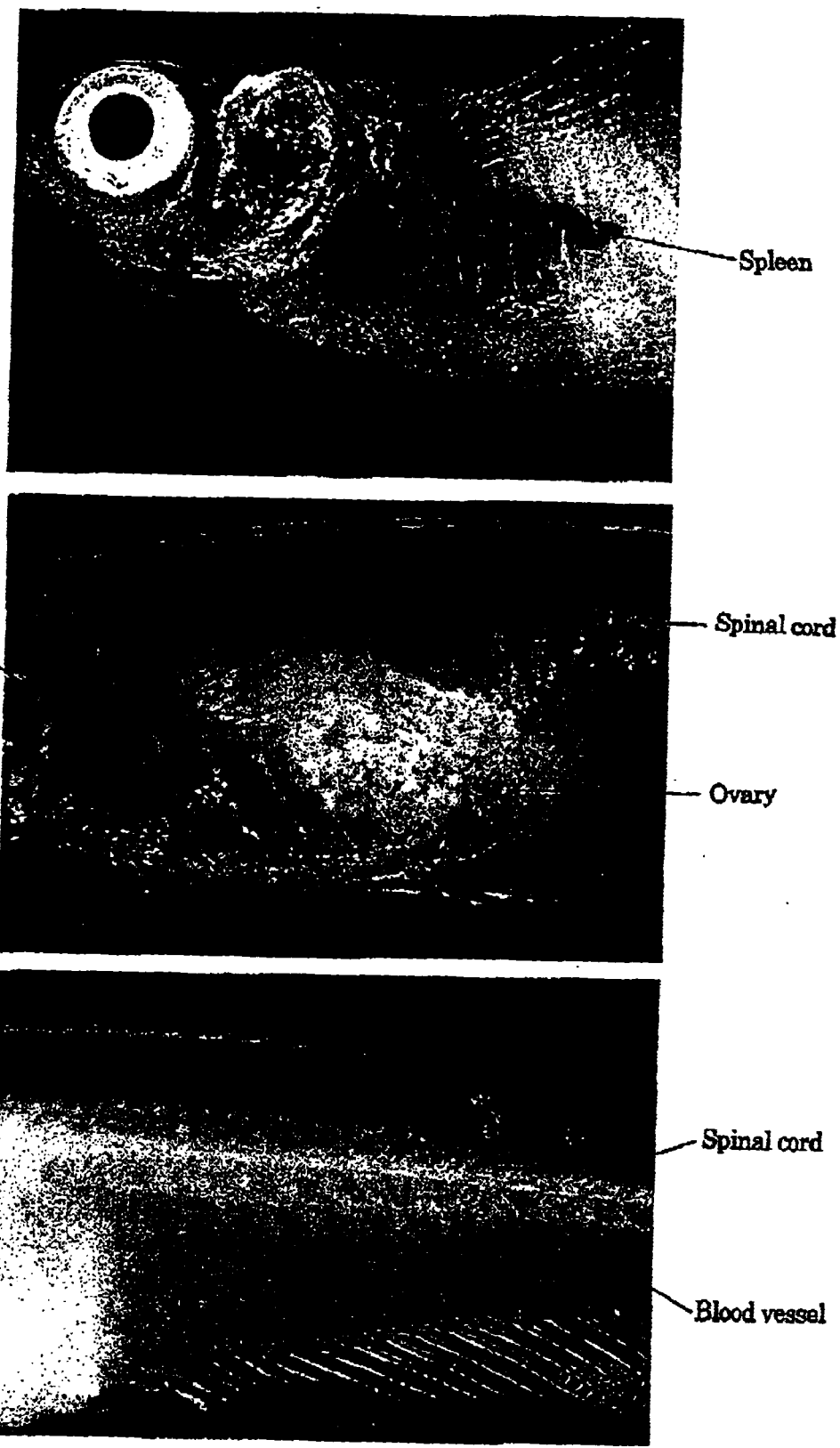
FIGS. 2A–B: Photographs of the see-through medaka of the present invention (STII strain), wherein a. shows organs seen through the body; b. shows dorsal view and ventral view.
Figure 2B:
Figure 2B:
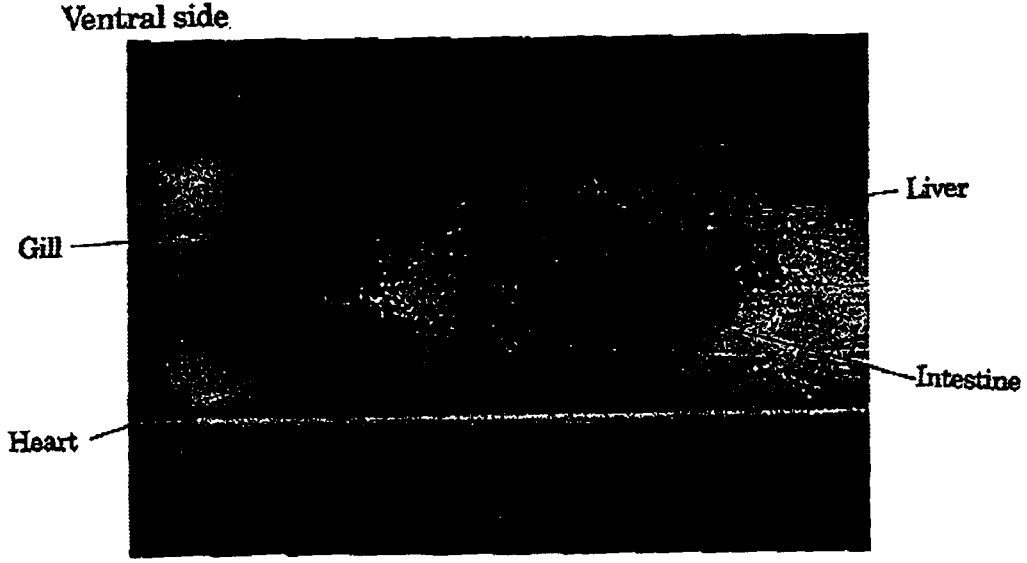

This medaka has no body color (i.e. see-through body wall and peritoneum), consequently, internal organs such as viscera and brain can be observed from the outside (FIG. 2). Hereinafter this see-through medaka strain is designated as "STII (See-through medaka II)".

(2) Production of STIII Strain

In order to obtain a further see-through medaka with a higher transparency level than the STII strain medaka obtained above, the STII strain and the body color mutant strain il-1 (specific properties of which are shown below and in Table 3) were mated as shown in the following Table 4. In the mating, two series of mating including the mating directions 1a→2a and 1b→2b were progressed in parallel.

$F_2$, female, having quadruple mutation was obtained from the mating in direction 1a→2a. Further, a similar $F_2$, male, was obtained from the mating in direction 1b→2b. The desired see-through medaka $F_3$ was obtained by mating with this male and female (mating No. 3).

(Specific Properties of the Strain)

STII: The See-Through Medaka of the Present Invention.

il-1: Less iridophore in the body surface and opercula. It was collected in Yamagata-City, in 1972, and deposited in the Bioscience Center, Nagoya Univ.

TABLE 3

Parental strains for mating

| Strain | Specific features | Genotype | Origin | Place of deposit | Furnishing |
|---|---|---|---|---|---|
| STII | See-through body wall and peritoneum | gu/gu, i-3/i-3, $X^{lf}/X(Y)^{lf}$ | Nagoya Univ. 2000 | Bioscience Center, Nagoya Univ. | Yes |
| il-1 | Less iridophore in body surface and opercula | il-i/il-1 | Yamagata-City, 1972 | Bioscience Center, Nagoya Univ. | Yes |

TABLE 4

Mating data

| Mating No. | Generation of Parents ♀ | Generation of Parents ♂ | Generation | Descendant Generation Genotype | Descendant Generation Phenotype |
|---|---|---|---|---|---|
| 1a | STII | il-1 | $F_1$-a | gu/+, i-3/+, il-1/+, $X^{lf}/X(Y)^+$ | $+^{gu}, +^{i-3}, +^{il-1}, +^{lf}$ |
| 2a | $F_1$-a | $F_1$-a | $F_2$-a | ♀: gu/gu, i-3/i-3, il-1/il-1, $X^{lf}/X^{lf}$ (1/256 of $F_2$, only ♀) | gu, i-3, il-1, lf (♀) |
| 1b | il-1 | STII | $F_1$-b | gu/+, i-3/+, il-1/+, $X^+/X(Y)^{lf}$ | $+^{gu}, +^{i-3}, +^{il-1}, +^{lf}$ |
| 2b | $F_1$-b | $F_1$-b | $F_2$-b | ♂: gu/gu, i-3/i-3, il-1/il-1, $X^{lf}/Y^{lf}$ (1/256 of $F_2$, only ♂) | gu, i-3, il-1, lf (♂) |
| 3 | $F_2$-a | $F_2$-b | $F_3$ | gu/gu, i-3/i-3, il-1/il-1, $X^{lf}/X(Y)^{lf}$ (all individuals) | gu, i-3, il-1, lf |

(Results)

In the $F_3$ generation, a see-through medaka having specific properties of ST-II strain and il-1 strain (genotype; gu/gu, i-3/i-3, il-1/il-1, $X^{lf}/X(Y)^{lf}$ and phenotype: gu, i-3, il-1, lf) was obtained.

This medaka has less iridophores than the STII strain, and has slightly higher transparency level of the body wall, peritoneum and opercula. In addition, there is not much reflection of light from the body surface. Consequently, observation of internal organs can be made more clearly. Hereinafter, this medaka strain is designated as "STIII (See-through medaka III)".

Furthermore, the four strains of body color mutant (gu, i-3, lf, il-1) used in the example, were found and collected in different areas in Japan several decades ago, as mentioned above, and since then they have not been found in anywhere in the world. Accordingly, mating between these three (gu, i-3, lf) or tour (gu, i-3, lf, il-1) strains would hardly ever occur in the realm of nature, therefore it is incapable of producing the medaka strains (STII and STIII) of the invention by essentially biological process.

Example 2

Production of see-through medaka for which sex identification can be easily performed In experiments involving in reproduction (for example, an experiment on the effect of endocrine disrupting chemicals), it is necessary to identify the sex of an experimental animal within the early stages of ontogeny and without error. Sexing of medaka is conventionally performed with reference to morphology of anal fin and dorsal fin, a papillary process on the anal fin of male, ovipositional behavior and body color (d-rR strain). These methods have problems with the number of days after hatching that is required before sexing is possible: in the case of observing morphology of fin or papillary process, a long term of 1.5–2.5 months is required; in the case of ovipositional behavior, 2–3 months are required; and in the case of observing body color in the d-rR strain, 2–3 weeks are required.

We have produced, according to the method described below, a see-through medaka, for which rapid sex identification is possible.

(1) Production of STII-YI Strain

STII strain produced by the process in example 1 and a strain, FLF, produced by mating with leucophore mutant lf and wild type at Nagoya Univ. in 2000 (specific properties are shown below and in Table 5) were used as mating parents, and these were mated as shown in Table 6 below.

(Specific Properties of Strains)

STII: The see-through medaka of the present invention.

FLF: This was produced by mating between leucophore mutant lf hereinabove and the wild type at Nagoya Univ. in 2000. Since lf gene is located on the X chromosome in this strain, the female lacks leucophores. Since the lf gene locus of the Y chromosome is wild type, the male has leucophores. Further, medaka of this strain has a sex-specific DNA (PCR) marker (SL1). SL1 is a base sequence positioned closely to the male sex determination factor on the Y chromosome and it is thought that its homologous region is located on the X chromosome. In this marker, a polymorphism is known. Since in the FLF strain, it is shorter on the Y chromosome than on the X chromosome, two bands (L) and (H) derived from Y chromosome and X chromosome, respectively, in the male and a single band (H) derived from X chromosome in the female are detected in PCR. On the other hand, in the above STII strain, SL1 has no difference between the X chromosome and the Y chromosome, therefore a single band is detected in both sexes, male and female, in PCR. The SL1 has also no difference from that of the X chromosome in FLF strain [i.e. (H)]. As shown in Table 6 hereinbelow, by means of selective mating, the Y chromosome of FLF strain was introduced into the $F_1$ generation to introduce SL1(L) [On details of SL1, refer to Matsuda, M. et al., Isolation of a sex chromosome-specific DNA sequence in the medaka, *Oryzias latipes*. Genes Genet. Syst. 72, 263–268 (1997)]. No errors were known for sex identification by this marker up to now (i.e. error=0).

TABLE 5

Parental strains for mating

| Strain | Specific features | Genotype | Origin | Place of Deposit | Furnishing |
|---|---|---|---|---|---|
| STII | see-through body wall and peritoneum | gu/gu, i-3/i-3, $X^{lf, H}/X(Y)^{lf, H}$ | Nagoya Univ. 2000 | Bioscience Center, Nagoya Univ. | Yes |
| FLF | Female: deficient in leucophore, single SL1 male: with leucophore, double SL1 | ♀: $X^{lf, H}/X^{lf, H}$ ♂: $X^{lf, H}/Y^{+, L}$ | Nagoya Univ. 2000 | Bioscience Center, Nagoya Univ. | Yes |

TABLE 6

Mating data

| Mating No. | Generation of parents ♀ | Generation of parents ♂ | Generation | Genotype | Phenotype |
|---|---|---|---|---|---|
| 1 | STII | FLF | $F_1$ | ♀: gu/+, i-3/+, $X^{lf,H}/X^{lf, H}$ ♂: gu/+, i-3/+, $X^{lf, H}/Y^{+, L}$ | ♀: $+^{gu}, +^{i-3}$, lf, H ♂: $+^{gu}, +^{i-3}, +^{lf}$, H/L |
| 2 | STII | $F_1$ | $F_2$ | ♀: gu/gu, i-3/i-3, $X^{lf, H}/X^{lf, H}$ ♂: gu/gu, i-3/i-3, $X^{lf, H}/Y^{+, L}$ (1/4 of $F_2$) | ♀: gu, i.3, lf, H ♂: gu, i-3, $+^{lf}$, H/L |
| 3 | $F_2$ | $F_2$ | $F_3$ | ♀: gu/gu, i-3/i-3, $X^{lf, H}/X^{lf, H}$ ♂: gu/gu, i-3/i-3, $X^{lf, H}/Y^{+, L}$ (all individuals) | ♀: gu, i-3, lf, H ♂: gu, i-3, $+^{lf}$, H/L |

(Results)

In the $F_3$ generation, a see-through medaka having specific properties of both of STII strain and FLF strain (phenotype: female: gu, i-3, lf, H and male: gu, i-3, $+^{lf}$, H/L) was obtained. The transparency level was slightly inferior in the male due to presence of leucophores, but was the same as the transparency level of STII in female. Hereinafter, this medaka strain is designated as "STII-YI".

Genetic sex of this medaka was identified by the presence of leucophores in the two-day-old embryo. Further, genetic sex was confirmed by using a DNA marker (SLl).

FLFW.$Y^{HNI}$ strain [The strain has three identification markers of genetic sexuality. One is the presence or absence of leucophores (present in ♂/absent in ♀); the second is body color (yellowish orange for ♂/white for ♀); and the third is SL1 marker (♂: two bands/♀: single band). Unpublished] was used as control. A part of the tail fin of an adult fish was cut, and DNA was extracted using a conventional method [nucleic acid extraction agent SepaGene (Sanko Pure Chemicals)]. PCR was conducted using 2 primers for SL1 detection [forward primer pHO5.5-F (5'-CCTGCAATGGGAAATTATTCTGCTC-3': SEQ ID NO: 1), reverse primer pHO5.5-RV (5'-CTTTTGTGTCTTTGGTTATGAAACGATG-3': SEQ ID NO: 2)] under the conditions shown in Table 7 and Table 8 below.

Figure 3A:
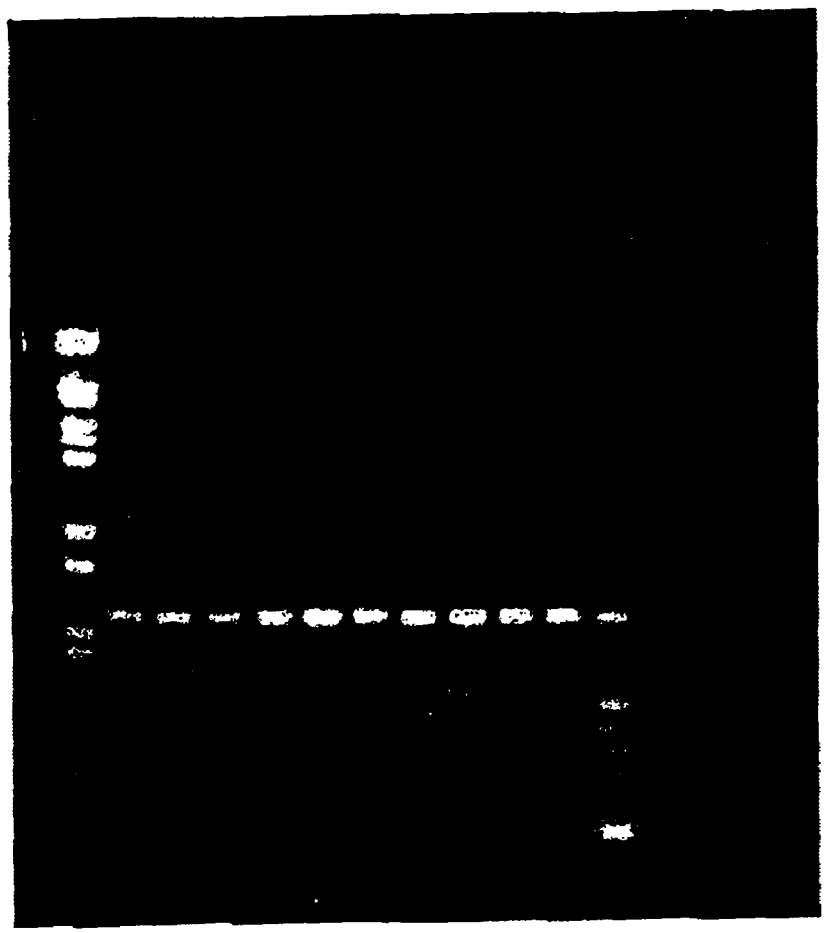
FIG. 3a: Result of an electrophoresis on DNA of STII-YI see-through medaka, female. Lane 1 and 12 indicate size markers of DNA; lanes 2 to 7 indicate an individual female of the other strain (FLFW.$Y^{HNI}$); and lanes 8–11 indicate four individual females (A, B, C and D) of STII-YI strain.

Results of electrophoresis of PCR products using 1% agarose gel/TBE are shown in FIGS. 3a (female) and b (male). Samples used in each lane are shown in Table 9 hereinbelow. A sample of λ-BstP I digest of bacteriophageλc1857Sam7 (Takara) and 100 bp DNA ladder (Takara) used as DNA markers are DNA size markers for confirmation of 1.3 kb band (1371 bp of λ-BstP I) and 1.5 kb band (1500 bp of 100 bp DNA ladder), respectively.

TABLE 7

Composition of the reaction mixture

| | μL/Sample | Final Concentration |
|---|---|---|
| $H_2O$ | 6.15 | |
| 10× buffer solution | 1.0 | |
| $MgCl_2$ (25 mM) | 0.6 | 1.5 mM |
| dNTP mixture (2.5 mM) | 0.8 | 0.2 mM |
| Primer pH05.5-F (10 pmol) | 0.2 | 0.2 μM |
| Primer pH05.5-RV (10 pmol) | 0.2 | 0.2 μM |
| Sample DNA (10–20 ng/μL) | 1.0 | |
| LA Taq (5 U/μL, Takara) | 0.05 | 0.25 U/10 μL |
| Total | 10.0 | |

TABLE 8

PCR conditions

| | Temperature (° C.) | Time (min.) |
|---|---|---|
| Heat denaturation | 95 | 5 |
| | 27 cycles | |
| Heat denaturation | 95 | 1.5 |
| Annealing | 63 | 1.5 |
| Elongation | 72 | 1.5 |
| Elongation | 72 | 5 |
| Storage | 4 | |

Thermal cycler: Gene Amp PCR system 2400-R (Perkin Elmer)

TABLE 9

Figure 3B:
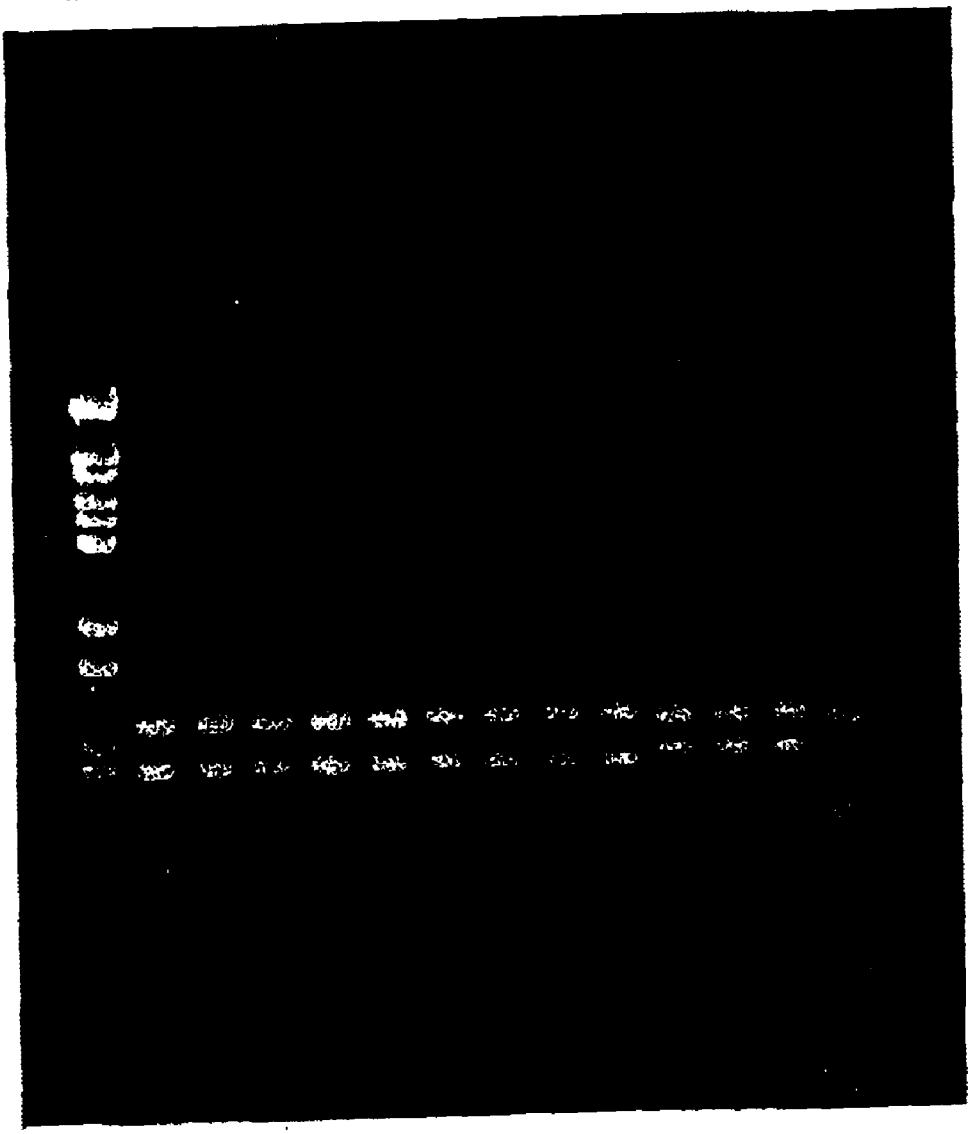
FIG. 3b: Result of an electrophoresis on DNA of STII-YI see-through medaka, male. Lane 1 and 14 indicate size markers of DNA; lanes 2 to 10 indicate an individual male of another strain (FLFW.$Y^{HNI}$); and lanes 11 to 13 indicate three individual males (C, D and E) of STII-YI strain.

Samples used in each lane in FIG. 3 a and b

| | Sample | |
|---|---|---|
| Lane | FIG. 3 a (female) Strain and Sample No. | FIG. 3 b (male) Strain and Sample No |
| 1 | λ-BstP I Digestion (Takara)[*1] | λ-BstP I Digestion (Takara)[*1] |
| 2 | FLFW.$Y^{HNI}$ strain 128 | FLFW.$Y^{HNI}$ strain 154 |
| 3 | 129 | 155 |
| 4 | 130 | 156 |
| 5 | 131 | 157 |
| 6 | 132 | 158 |
| 7 | 133 | 159 |
| 8 | STII-YI strain A | 160 |
| 9 | B | 161 |
| 10 | C | 162 |
| 11 | D | STII-YI strain C |
| 12 | 100 bp DNA ladder (Takara)[*2] | D |
| 13 | | E |
| 14 | | 100 bp DNA ladder (Takara)[*2] |

[*1]λBstP I digestion (Takara): DNA size marker which is digested bacteriophageγc1857Sam7 by enzyme BstPI (Takara).
[*2]100 bp DNA ladder (Takara): DNA size marker.

Results

According to the result of electrophoresis shown in, FIG. 3, two bands in all of male medaka and one band in all female medaka were detected.

(2) Production of STII-YII Strain

Since a male of STII-YI medaka strain obtained in (1) above has leucophores, its transparency level is lower than that of a female. To improve this point, a see-through strain without leucophores in both male and female were produced.

A female of STII strain and a male of the leucophore deficient (lf) [STII-YI (1f)] strain (speciic properties of each strain are described below and shown in Table 10), which was generated by the crossing-over of the X chromosome and the Y chromosome in the above STII-YI strain, were used as parental strains for mating as shown in the following Table 11.

(Specific Properties of Strains)

STII: The See-Through Medaka of the Present Invention.

STII-YI: Leucophore deficient (lf) male generated by crossing-over of X chromosome and Y chromosome in STII-YI strain.

TABLE 10

Parental strains for mating

| Strain | Specific Features | Genotype | Origin | Place of Deposit | Furnishing |
|---|---|---|---|---|---|
| STII female | See-through body wall and peritoneum | ♀: gu/gu, i-3/i-3, $X^{lf,H}/X^{lf,H}$ | Nagoya Univ. 2000 | Bioscience Center, Nagoya Univ. | Yes |
| STII-YI male of lf, generated by crossing-over of sex chromosomes | See-through body wall and peritoneum, possible for descrimination genetic sexuality | ♂: gu/gu, i-3/i-3, $X^{lf,H}/Y^{lf,L}$ | Nagoya Univ. 2000 | Bioscience Center, Nagoya Univ. | Yes |

TABLE 11

Mating data

| Mating No. | Generation of Parents ♀ | ♂ | Descendant Generation Generation | Genotype | Phenotype |
|---|---|---|---|---|---|
| 1 | STII | STII-YI (lf) | $F_1$ | ♀: gu/gu, i-3/i-3, $X^{lf,H}/X^{lf,H}$ ♂: gu/gu, i-3/i-3, $X^{lf,H}/Y^{lf,L}$ (all individuals) | ♀: gu, i-3, lf, H ♂: gu, i-3, lf, H/L |

(Results)

In the $F_1$ generation, the see-through medaka having specific properties of STII and STII-YI strains (phenotype: female: gu, i-3, lf, H and male: gu, i-3, lf, H/L) was obtained, Transparency level of male and female was the same as that of STII. Hereinafter this medaka strain is designated as "STII-YII".

Sex identification of these medaka was performed by detecting SL1 band of DNA marker by PCR as in STII-YI of (1) above (data not shown).

(3) Production of STII-YI Strain

We have further studied in order to produce a strain, which has a higher transparency level of the body wall, peritoneum and opercula than that of STII-YI strain. STIII strain was used as a parent strain in place of STII strain, and this was mated with STII-YI obtained in (1) above (specific properties are shown in Table 12) as shown in the following Table 13.

TABLE 12

Parental strains for mating

| Strain | Specific Features | Genotype | Origin | Place of Deposit | Furnishing |
|---|---|---|---|---|---|
| STIII female | See-through body wall, peritoneum and opercula | ♀: gu/gu, i-3/i-3 il-1/il-1, $X^{lf,H}/X^{lf,H}$ | Nagoya Univ. 2000 | Bioscience Center, Nagoya Univ. | Yes |
| STII-YI male | See-through body wall and peritoneum, with genetic sexual marker | ♀: gu/gu, i-3/i-3, $X^{lf,H}/Y^{+,L}$ | Nagoya Univ. 2000 | Bioscience Center, Nagoya Univ. | Yes |

TABLE 13

Mating data

| Mating No. | Generation of Parents ♀ | ♂ | Descendant Generation Generation | Genotype | Phenotype |
|---|---|---|---|---|---|
| 1 | STIII | STII-YI | $F_1$ | ♀: gu/gu, i-3/i-3, il-1/+, $X^{lf,H}/X^{lf,H}$ ♂: gu/gu, i-3/i-3, il-1/+, $X^{lf,H}/Y^{+,L}$ | ♀: gu, 1-3, $+^{il-1}$, lf, H ♂: gu, 1-3, $+^{il-1}$, $+^{lf}$, H/L |
| 2 | STIII | | $F_1$ $F_2$ | ♀: gu/gu, i-3/i-3, il-1/il-1, $X^{lf,H}/X^{lf,H}$ ♂: gu/gu, i-3/i-3, il-1/il-1, $X^{lf,H}/Y^{+,L}$ (1/2 of $F_2$) | ♀: gu, i-3, il-1, lf, H ♂: gu, i-3, il-1, $+^{lf}$, H/L |
| 3 | $F_2$ | $F_2$ | $F_3$ | ♀: gu/gu, i-3/i-3, il-1/il-1, $X^{lf,H}/X^{lf,H}$ ♂: gu/gu, i-3/i-3, il-1/il-1, $X^{lf,H}/Y^{+,L}$ (all individuals) | ♀: gu, i-3, il-1, lf, H ♂: gu, i-3, il-1, $+^{lf}$, H |

(Results)

In the $F_3$ generation, a see-through medaka having specific properties of STIII and STII-YI strains (phenotype: female: gu, i-3, il-1, lf, H and male: gu, i-3, il-1, $+^{lf}$, H/L) was obtained. The genetic sex of this medaka was identified by the presence of leucophores in the two-day-old embryo as with the STII-YI strain. Further, genetic sex was confirmed by a DNA marker (SL1) using DNA isolated from the tail fin of an adult fish. In this strain, the transparency level was slightly reduced due to the presence of leucophores in the male, but the same transparency level as STIII was obtained in the female. Hereinafter this strain is designated as "STIII-YI".

(4) Production of STIII-YII Strain

Since the male of STIII-YI strain obtained in the (3) above has leucophores, its transparency level is lower than that of the female. In order to improve this point, a strain without leucophores in the male and female was produced.

STIII strain (aforementioned, example 1 (2)), female, was used as the parental strain, and this was mated with the leucophore deficient (lf) male [STIII-YI(lf)] generated by crossing-over of the X chromosome and Y chromosome in the above STIII-YI strain (specific properties are shown in Table 14) as shown in Table 15 hereinbelow.

TABLE 14

Parental strains for mating

| Strain | Specific Features | Genotype | Origin | Place of Deposit | Furnishing |
|---|---|---|---|---|---|
| STIII female | See-through body wall, peritoneum and opercula | ♀: gu/gu, i-3/i-3, il-1/il-1, X$^{lf,H}$/X$^{lf,H}$ | Nagoya Univ. 2000 | Bioscience Center, Nagoya Univ. | Yes |
| STIII-YI strain male of lf, generated by crossing-over of sex chromosomes | See-through body wall, peritoneum, and opercula, with genetic sexual marker | ♂: gu/gu, i-3/i-3, il-1/il-1, X$^{lf,H}$/Y$^{lf,L}$ | Nagoya Univ. 2000 | Bioscience Center, Nagoya Univ. | Yes |

TABLE 15

Mating data

| | Generation of Parents | | Descendant Generation | | |
|---|---|---|---|---|---|
| Mating No. | ♀ | ♂ | Generation | Genotype | Phenotype |
| 1 | STIII | STIII-YI (lf) | F$_1$ | ♀: gu/gu, i-3/i-3, il-1/il-1, X$^{lf,H}$/X$^{lf,H}$ ♂: gu/gu, i-3/i-3, il-1/il-1, X$^{lf,H}$/Y$^{lf,L}$ (all individuals) | ♀: gu, 1.3, il-1, lf, H ♂: gu, i-3, il-1, lf, H/L |

(Results)

In the F$_1$ generation, a see-through medaka having specific properties of STIII and STIII-YI (phenotype: female: gu, i-3, il-1, lf, H, and male; gu, i-3, il-1, lf, H/L) was obtained. The transparency level was almost the same as STIII in the female and male. Hereinafter, this strain is designated as "STIII-YI".

Sex identification of these medaka was performed by detecting bands of a DNA marker (SL1) by PCR as with the STII-YI strain of (1) above (data not shown).

Example 3

Production of a see-through medaka characterized by the production of luminescence in the gonadal tissue (germ cells)

We have produced a strain, in which vasa-GFP fluorescence in gonadal tissues (germ cells) can be observed not only in the early stages of the individual but also throughout its lifetime, by introducing a hybrid gene, which was prepared by fusing a promoter region of a vasa gene which specifically expresses in the germ cells with the coding region of GFP (green fluorescent protein: protein of *Aequorea victoria* and emitting green fluorescence by irradiating blue light) gene, into the see-through medaka of the present invention.

At first, medaka ovaries were frozen with liquid nitrogen and crushed to homogenize. Then whole RNA was purified, and mRNA was further purified, then cDNA was synthesized using this as a template. This was inserted into a vector and packaged into a phage to prepare an ovary cDNA library (Shinomiya, Ai, Tanaka, Minoru, Kobayashi, Tohru and Hamaguchi, Tetsu, "Identification and migration route of primordial germ cells of medaka using expression of vasa homologous gene as an indicator," Proceedings of the 32nd Annual Meeting of the Japan Society of Developmental Biologists, page 56, 1999). Medaka vasa cDNA was isolated from this library.

The fact that vasa protein has DEAD Box, which is an RNA binding domain, and this region is conserved among animals is known. Thus, primers common to animals in this region [forward primer-1: 5'-ATGGCNTG(T/C)GCNCA(A/G)ACNG-3' (SEQ ID NO: 3) and reverse primer-2: 5'-(A/G)AANCCCAT(A/G)TC(T/C)AACAT-3' (SEQ ID NO: 4)] were designed. PCR was performed using whole cDNA library of medaka as a template (94° C. for 10 min., 94° C. for 30 sec., 55° C. for 1 min., 72° C. for 1 min. for one cycle, total 39 cycles). Amplified vasa cDNA short fragment was purified by agarose gel for cloning. After confirming the fragment as medaka vasa cDNA by nucleotide sequencing determination, screening of the medaka cDNA library was performed again using the fragment as probe.

As a result, full length cDNAs, which were thought to contain the entire amino acid coding region, were isolated for cloning. The medaka vasa cDNA was confirmed by determination of nucleotide sequencing (Proceedings of the 32nd Annual Meeting of the Japan Society of Developmental Biologists, aforementioned).

Next, the medaka vasa-GFP gene was constructed. The vasa-GFP gene was a hybrid gene, in which the promoter region of medaka vasa gene (olvas) was fused with the coding region of GFP gene. 3' region of the medaka vasa gene (olvas) was amplified using 2 primers (T7; 5'-TAATACGACTCACTATAGGG-3': SEQ ID NO: 5, and VI-8; 5'-AGGAGGTGCCGTCATGGCTGGAG-3': SEQ ID NO: 6) with a template of cloned DNA [XLE13; 3' site of medaka vasa gene (olvas)].

The thus obtained fragment was cleaved with restriction enzymes PstI/EcoTI, and the termini were blunt-ended with T4 DNA polymerase. This fragment was cloned to the StuI restriction site of GFP vector (pEGFP: CLONTECH Inc., 1020 East Meadow Circle, Palo Alto, Calif., USA) and the resulting fragment was designated as pEGPP-3V.

Further, a 5.1 kb genomic fragment containing the vasa gene (olvas) promoter region was amplified using primers (VP1M; 5'-CCTCCCAGTCGTCCATATGAATCGTCTGAT-3': SEQ ID NO: 7, and VP3; 5'-AGAGGATCCAATAGAATGAGTAATGGTTCTCTA TTTC-3': SEQ ID NO: 8) with phage DNA [V5; containing most part of medaka vasa gene (olvas)] as a template. The thus obtained fragment was cleaved with NdeI; blunt-ended with T4 DNA polymerase, and further cleaved with KpnI. This fragment was cloned to KpnI/blunt end of NcoI site of pEGFP-3V vector to prepare a vector. (VEGFPA) for gene transfer. Since the GFP gene was commercially available, this was purchased for use (CLONTECH Inc., 1020 East Meadow Circle, Palo Alto, Calif., USA).

Fertilized eggs of himedaka were collected after 30 minutes of oviposition and attached filaments were removed using forceps. The above vector VEGFPA was injected into the cytoplasm of the one-cell-stage embryo by microinjection. The injected eggs were kept at 25° C. and expression of GFP fluorescence was observed by fluorescence stereoscopic microscope. The embryo and fry expressing GFP fluorescence were separated and raised to adulthood. Sexually mature individuals were paired with normal individuals (without gene injection) and mated to obtain embryos of the next generation ($F_1$). These were searched for GFP fluorescence and GFP gene by PCR. By this operation, parent individuals ($F_0$) who transmitted the GFP gene to their progeny were identified. The progeny ($F_1$) from these parent individuals were mated to produce vasa-GFP transgenic medaka [in detailed operation, refer to Keiko Hamada et al. "Usefulness of the medaka β-actin promoter investigated using a mutant GFP reporter gene in transgenic medaka (*Oryzias latipes*)", Mol Marine Biol Biotech (1998) 7(3), 173–180; Tanaka Minoru et al., The 22nd Annual Meeting of the Molecular Biology Society, Program, Abstract, aforementioned]. This strain is designated as "vasa-GFP" (which can be furnished from the Div. Biological Sciences, Graduate School of Science, Hokkaido Univ.).

(1) Production of STII-YI-vasa-GFP Strain

A male of the above vasa-GFP strain, a male and female of STII strain of the present invention and a male of STII-YI strain (specific properties of each strain are shown in Table 16) were used as parental strains for mating and subjected to repeated selective mating as shown in Table 17 hereinbelow.

TABLE 16

Parental strains for mating

| Strain | Specific Features | Genotype | Origin | Place of Deposit | Furnishing |
|---|---|---|---|---|---|
| vasa-GFP male | germ cells with green fluorescence | vasa-GPP/—, $X^{+,H}/Y^{+,H}$ | National Institute for Basic Biology and Kyoto Univ. 2000 | Div. Biological Sciences, Graduate School of Science, Hokkaido Univ. | Yes |
| STII female and male | see-through body wall and peritoneum | gu/gu, i-3/i-3, $X^{1f,H}/X(Y)^{1f,H}$ | Nagoya Univ. 2000 | Bioscience Center, Nagoya Univ. | Yes |
| STII-YI male | see-through body wall and peritoneum possible for discrimination of genetic sexuality | gu/gu, i-3/i-3, $X^{1f,H}/Y^{+,L}$ | Nagoya Univ. 2000 | Bioscience Center, Nagoya Univ. | Yes |

TABLE 17

Mating data

| Mating No. | Generation of parents ♀ | Generation of parents ♂ | Descendent Generation | Genotype | Phenotype |
|---|---|---|---|---|---|
| 1 | STII | vasa-GFP | $F_1$ | gu/+, i-3/+, vasa-GFP/—, $X^{1f,H}/X(Y)^{+,H}$ (1/2 of $F_2$) | $+^{gu}$, $+^{i-3}$, vasa-GFP, $+^{1f}$, H |
| 2 | $F_1$ | STII | $F_2$ | gu/gu, i-3/i-3, vasa-GFP/—, $X^{1f,H}/X(Y)^{1f,H}$ (1/16 of $F_2$) | gu, i-3, vasa-GFP, 1f, H |
| 3 | $F_2$ | STII-YI | $F_3$ | ♀: gu/gu, i-3/i-3, vasa-GFP/—, $X^{1f,H}/X^{1f,H}$ ♂: gu/gu, i-3/i-3, vasa-GFP/—, $X^{1f,H}/Y^{+,L}$ (1/2 of $F_3$) | ♀: gu, i-3, vasa-GFP, 1f, H ♂: gu, i-3, vasa-GFP, $+^{1f}$, H/L |
| 4 | $F_3$ | $F_3$ | $F_4$ | ♀: gu/gu, i-3/i-3, vasa-GFP/ vasa-GFP, $X^{1f,H}/X^{1f,H}$ ♂: gu/gu, i-3/i-3, vasa-GFP/ vasa-GFP, $X^{1f,H}/Y^{+,L}$ (1/4 of $F_3$) | ♀: gu, 1-3, vasa-GFP, 1f, H ♂: gu, i-3, vasa-GFP, $+^{1f}$, H/L |
| 5 | $F_4$ | $F_4$ | $F_5$ | ♀: gu/gu, i-3/i-3, vasa-GFP/ vasa-GFP, $X^{1f,H}/X^{1f,H}$ ♂: gu/gu, i-3/i-3, vasa-GFP/ vasa-GFP, $X^{1f,H}/Y^{+,L}$ (all individuals) | ♀: gu, i-3, vasa-GFP, 1f, H ♂: gu, i-3, vasa-GFP, $+^{1f}$, H/L |

(Results)

In the $F_5$ generation, a medaka which had all the specific properties of the three parental strains, vasa-GFP, STII and STII-YI (phenotype: female: gu, i-3, vasa-GFP, 1f, H, and male: gu, i-3, vasa-GFP, $+^{1f}$, H/L), was obtained. Genetic sex was identified as in example 2 (1) by leucophores and a DNA marker (SL1). The transparency level of the male was slightly inferior due to existence of leucophores and that of the female was the same as that of STII. Hereinafter this strain was designated as "STII-YI-vasa-GFP".

Since this medaka has a see-through body, the behavior of germ cells producing fluorescence can be observed throughout the lifetime of the individual not only in the embryonic stage but also in the process of growth after hatching to adulthood.

(2) Production of STII-YII-vasa-GFP strain

Since a male medaka of STII-YI-vasa-GFP strain obtained in (1) above has leucophores, the transparency level is lower when compared with that of the female. In order to improve this point, a strain without leucophores in the male and female was produced.

A female of the above STII-YI-vasa-GFP strain and a male of the leucophore deficient (1f) [STII-YI-vasa-GFP (1f)] strain generated by crossing-over of the X chromosome and the Y chromosome in the above STII-YI-vasa-GFP strain (specific properties of each strain are shown in Table 18), were mated as shown in Table 19 below.

TABLE 18

Parental strains for mating

| Strain | Specific Features | Genotype | Origin | Place of Deposit | Furnishing |
|---|---|---|---|---|---|
| STII-YI-vasa-GFP female | see-through body wall and peritoneum. luminescent in gonadal tissues (germ cells). possible for discrimination of genetic sexuality | gu/gu, i-3/i-3, vasa-GFP/vasa-GFP, $X^{lf,H}/X^{lf,H}$ | Nagoya Univ. | Bioscience Center. Nagoya Univ. | Yes |
| STII-YI-vasa-GFP male of lf, generated by crossing-over of sex chromosomes | see-through body wall and peritoneum. luminescent in gonadal tissues (germ cells). possible for discrimination of genetic sexuality | gu/gu, i-3/i-3, vasa-GFP/vasa-GFP, $X^{lf,H}/X^{lf,H}$ | Nagoya Univ. | Bioscience Center. Nagoya Univ. | Yes |

TABLE 19

Mating data

| Mating No. | Generation of Parents ♀ | Generation of Parents ♂ | Generation | Descendant Genotype | Descendant Phenotype |
|---|---|---|---|---|---|
| 1 | STII-YI-vasa-GFP | STII-YI-vasa-GFP (lf) | $F_1$ | ♀: gu/gu, i-3/i-3, vasa-GFP/vasa-GFP, $X^{lf,H}/X^{lf,H}$<br>♂: gu/gu, i-3/i-3, vasa-GFP/vasa-GFP, $X^{lf,H}/Y^{lf,L}$<br>(all individuals) | ♀: gu, i-3, vasa-GFP, lf, H<br>♂: gu, i-3, vasa-GFP, lf, H/L |

(Results)

In the $F_1$ generation, a medaka having specific properties of the two types of parental strains, STII-YI-vasa-GFP and STII-YI-vasa-GFP (lf) was obtained. Genetic sex was identified by DNA marker (SL1) as in example 2 (1). Transparency levels of the female and male were the same as those of STII. Hereinafter this strain was designated as "STII-YII-vasa-GFP".

Since this medaka has a see-through body wall and peritoneum and a gonadal tissues (germ cells) producing luminescence, the behavior of germ cells can be observed throughout the lifetime of the individuals not only in the embryonic stage but also in the process of growth after hatching to adulthood.

(3) Production of STIII-YI-vasa-GFP Strain

We have further studied in order to produce a strain, which has a higher transparency level of the body wall, peritoneum and opercula than the STII-YI-vasa-GFP strain. A female of STIII strain (aforementioned, example 1 (2)) was used as a parent strain in place of STII strain, and this was selectively and repeatedly mated with a male of STII-YI-vasa-GFP strain obtained in (1) above (specific properties of each strain are shown in Table 20) as shown in the following Table 21.

TABLE 20

Parental strains for mating

| Strain | Specific Features | Genotype | Origin | Place of Deposit | Furnishing |
|---|---|---|---|---|---|
| STIII female | See-through body wall, peritoneum and opercula | gu/gu, i-3/i-3, il-1/il-1, $X^{lf,H}/X^{lf,H}$ | Nagoya Univ. 2000 | Bioscience Center, Nagoya Univ. | Yes |
| STII-YI-vasa-GFP male | See-through body wall, peritoneum and opercula luminescent in gonadal tissues (germ cells), possible for discrimination of genetic sexuality | gu/gu, i-3/i-3, vasa-GFP/vasa-GFP, $X^{lf,H}/Y^{+,L}$ | Nagoya Univ. 2000 | Bioscience Center, Nagoya Univ. | Yes |

TABLE 21

Mating data

| Mating No. | Generation of Parents ♀ | Generation of Parents ♂ | Generation | Descendant Genotype | Descendant Phenotype |
|---|---|---|---|---|---|
| 1 | STIII | STII-YI-vasa-GFP | $F_1$ | ♀: gu/gu, i-3/i-3, il-1/+, vasa-GFP/−, $X^{lf,H}/X^{lf,H}$<br>♂: gu/gu, i-3/i-3, il-1/+, vasa-GFP/−, | ♀: gu, i-3, $+^{il-1}$, vasa-GFP, lf, H<br>♂: gu, i-3, $+^{il-1}$, vasa-GFP, $+^{lf}$, H/L |

TABLE 21-continued

| | Generation of Parents | | Descendant Generation | | |
|---|---|---|---|---|---|
| Mating No. | ♀ | ♂ | Generation | Genotype | Phenotype |
| 2 | $F_1$ | $F_1$ | $F_2$ | ♀: gu/gu, i-3/i-3, il-1/il-1, vasa-GFP/vasa-GFP, $X^{lf,H}/X^{lf,H}$ ♂: gu/gu. i-3/i-3, il-1/il-1, vasa-GFP/vasa-GFP, $X^{lf,H}/Y^{+,L}$ (1/16 of $F_2$) | ♀: gu, i-3, il-1, vasa-GFP, lf, H ♂: gu, i-3, il-1, vasa-GFP, $+^{lf}$, H/L |
| 3 | $F_2$ | $F_2$ | $F_3$ | ♀: gu/gu, i-3/i-3, il-1/il-1, vasa-GFP/vasa-GFP, $X^{lf,H}/X^{lf,H}$ ♂: gu/gu. i-3/i-3, il-1/il-1, vasa-GFP/vasa-GFP, $X^{lf,H}/Y^{+,L}$ (all individuals) | ♀: gu, i-3, il-1, vasa-GFP, lf, H ♂: gu, i-3, il-1, vasa-GFP, $+^{lf}$, H/L |

(Results)

In the $F_3$ generation, medaka having specific properties of the two types of parental strains, STIII and STII-YI-vasa-GFP was obtained. Genetic sex was identified in the same way as in example 2 (1) by leucophores and a DNA marker (SL1). The transparency level of the male was slightly inferior due to existence of leucophores and that of the female was the same as that of STIII. Hereinafter this strain was designated as "STIII-YI-vasa-GFP".

This medaka has a high transparency level of body wall, peritoneum and opercula, and the gonadal tissues (germ cells) produce luminescence. Consequently, the behavior of germ cells can be observed throughout the lifetime of the individuals not only in the embryonic stage but also in the process of growth after hatching to adulthood.

(4) Production of STIII-YII-vasa-GFP Strain

Since STIII-YI-vasa-GFP strain medaka, male, obtained in (1) above has leucophores, the transparency level is lower when compared with that of the female. In order to improve this point, a strain without leucophores in the male and female was produced.

A female of the above STIII-YI-vasa-GFP strain and a male of the leucophore deficient (lf) [STIII-YI-vasa-GFP (lf)] strain generated by crossing-over of the X chromosome and the Y chromosome in the above STIII-YI-vasa-GFP strain (specific properties of each strain are shown in Table 22), were mated selectively and repeatedly as shown in Table 23 below.

TABLE 22

| | | Parental strains for mating | | | |
|---|---|---|---|---|---|
| Strain | Specific Features | Genotype | Origin | Place of Deposit | Furnishing |
| STIII-YI-vasa-GFP female | See-through body wall, peritoneum and opercula, luminescent in gonadal tissues (germ cells) possible for discrimination of genetic sexuality | gu/gu, i-3/i-3, il-1/il-1, vasa-GFP/ vasa-GFP, $X^{lf,H}/X^{lf,H}$ | Nagoya Univ. 2000 | Bioscience Center, Nagoya Univ. | Yes |
| STIII-YI-vasa-GFP male of lf, generated by crossing-over of sex chromosomes | See-through body wall, peritoneum and opercula, luminescent in gonadal tissues (germ cells) possible for discrimination of genetic sexuality | gu/gu, i-3/i-3, il-1/il-1, vasa-GFP/ vasa-GFP, $X^{lf,H}/Y^{lf,L}$ | Nagoya Univ. 2000 | Bioscience Univ. center, Nagoya Univ. | Yes |

TABLE 23

| | Generation of Parents | | Descendant Generation | | |
|---|---|---|---|---|---|
| Mating No. | ♀ | ♂ | Generation | Genotype | Phenotype |
| 1 | STIII-YI-vasa-GFP | STIII-YI-vasa-GFP (lf) | $F_1$ | ♀: gu/gu, i-3/i-3, il-1/il-1, vasa-GFP/vasa-GFP, $X^{lf,H}/X^{lf,H}$ | ♀: gu, i-3, il-1, vasa-GFP, if, H |
| | | | | ♂: gu/gu, i-3/i-3, il-1/il-1, vasa-GFP/vasa-GFP, $X^{lf,H}/Y^{lf,L}$ (all individuals) | ♀: gu, i-3, il-1, vasa-GFP, if, H/L |

(Results)

In the $F_1$ generation, a medaka having specific properties of the two types of parental strains, STIII-YI-vasa-GFP and STIII-YI-vasa-GFP (lf) was obtained. Genetic sex was discriminated by DNA marker (SLl) as the same way as in example 2 (1). Transparency levels of the female and male were the same as those of STIII. Hereinafter this strain was designated as "STIII-YII-vasa-GFP".

This medaka has a high transparency level of the body wall, peritoneum and opercula, and the gonadal tissues (germ cells) produce luminescence. Consequently, the behavior of germ cells can be observed throughout the lifetime of the individuals not only in the embryonic stage but also in the process of growth after hatching to adulthood.

Effects of the Invention

According to the present invention, a see-through medaka useful as a research resource for biology, medical sciences and fishery sciences, as an experimental animal for testing toxic chemicals, as a teaching material for science education in primary school, junior school and senior high school, and as an aquarium fish, can be provided.

Seqence Listing Free Text

SEQ ID NO.1: Forward primer pHO5.5-F.

SEQ ID NO.2: Reverse primer pHO5.5-RV.

SEQ ID NO.3: Common sequence found in animals. The sequence is used herein as a forward primer to amplify the short fragment of vasa cDNA.

SEQ ID NO.4: Common sequence found in animals. The sequence is used herein as a reverse primer to amplify the short fragment of vasa cDNA.

SEQ ID NO.5: Primer T7 used to amplify the 3' region of vasa gene.

SEQ ID NO.6: Primer VI-8 used to amplify the 3' region of vasa gene.

SEQ ID NO.7: Primer VP1M used to amplify 5.1 kb genomic fragment comprising the promotor region of vasa gene.

SEQ ID NO.8: Primer VP3 used to amplify 5.1 kb genomic fragment comprising the promotor region of vasa gene.

All publications, patents and patent applications cited herein are incorporated herein by reference in their entirety.

What is claimed is:

1. A see-through medaka wherein said medaka is deficient in iridophores, melanophores, xanthophores and leucophores.

2. The see-through medaka according to claim 1 wherein said medaka is produced by means of repeated selective mating between iridophore deficient mutant medaka strain gu, albino mutant medaka strain i-3 and leucophore deficient mutant medaka strain lf.

3. A see-through medaka wherein said medaka is produced by further selective mating between the see-through medaka according to claim 2 and iridophore deficient mutant medaka strain il-1.

4. A see-through medaka wherein said medaka is deficient in iridophores, melanophores and xanthophores, and wherein the sex of said medaka can be identified by the presence or absence of leucophores and/or a DNA marker.

5. The see-through medaka according to claim 4 wherein said medaka is produced by means of repeated selective mating between iridophore deficient mutant medaka strain gu, albino mutant medaka strain i-3, leucophore deficient mutant medaka strain lf and medaka FLF strain which is deficient in leucophores in the female.

6. A see-through medaka wherein said medaka is produced by further selective mating between the see-through medaka according to claim 3 and a see-through medaka produced by repeated selective mating between iridophore deficient mutant medaka strain gu, albino mutant medaka strain i-3, leucophore deficient mutant medaka strain lf, and medaka ELF strain which is deficient in leucophores in the female.

7. A transgenic see-through medaka deficient in iridophores, melanophores, xanthophores and leucophores, having in its genome a transgene being a fusion of a promoter of a gene which expresses specifically in a specific organ, with a coding region of a gene encoding a fluorescent protein, wherein said fluorescent protein is expressed specifically in said organ.

8. A transgenic see-through medaka produced by further selective mating between the see-through medaka according to claim 2 and an iridophore deficient mutant medaka strain il-1,
wherein a transgene being a fusion of a promoter of a gene which expresses specifically in a specific organ, with a coding region of a gene encoding a fluorescent protein, is introduced into the produced see-through medaka, and/or is carried by at least one of the see-through medaka according to claim 2 and the iridophore deficient mutant medaka strain il-1,
so that the transgenic see-through medaka has in its genome said transgene, and wherein said fluorescent protein is expressed specifically in said organ.

9. A transgenic see-through medaka deficient in iridophores, melanopores and xanthophores, wherein the sex of said medaka can be identified by the presence or absence of leucophores and/or a DNA marker, having in its genome a transgene being a fusion of a promoter of a gene which expresses specifically in a specific organ, with a coding region of a gene encoding a fluorescent protein, wherein said fluorescent protein is expressed specifically in said organ.

10. A transgenic see-through medaka produced by further selective mating between the see-through medaka according to claim 3 and a see-through medaka produced by repeated selective mating between iridophore deficient mutant medaka strain gu, albino mutant medaka strain i-3, leucophore deficient mutant medaka strain lf, and medaka FLF strain which is deficient in leucophores in the female,
wherein a transgene being a fusion of a promoter of a gene which expresses specifically in a specific organ, with a coding region of a gene encoding a fluorescent protein, is introduced into the produced see-through medaka, and/or is carried by at least one of the see-through medaka according to claim 3 and a see-through medaka produced by repeated selective mating between iridophore deficient mutant medaka strain gu, albino mutant medaka strain i-3, leucophore deficient mutant medaka strain lf, and medaka FLF strain which is deficient in leucophores in the female,
so that the transgenic see-through medaka has in its genome said transgene, and wherein said fluorescent protein is expressed specifically in said organ.

11. The transgenic see-through medaka according to claim 7 wherein said gene encoding the fluorescent protein is a gene encoding a green fluorescent protein.

12. The transgenic see-through medaka according to claim 8 wherein said gene encoding the fluorescent protein is a gene encoding a green fluorescent protein.

13. The transgenic see-through medaka according to claim 9 wherein said gene encoding the fluorescent protein is a gene encoding a green fluorescent protein.

14. The transgenic see-through medaka according to claim 10 wherein said gene encoding the fluorescent protein is a gene encoding a green fluorescent protein.

15. The transgenic see-through medaka according to claim 7 wherein said organ is a gonadal organ.

16. The transgenic see-through medaka according to claim 8 wherein said organ is a gonadal organ.

17. The transgenic see-through medaka according to claim 9 wherein said organ is a gonadal organ.

18. The transgenic see-through medaka according to claim 10 wherein said organ is a gonadal organ.

19. The transgenic see-through medaka according to claim 11 wherein said organ is a gonadal organ.

20. The transgenic see-through medaka according to claim 12 wherein said organ is a gonadal organ.

21. The transgenic see-through medaka according to claim 13 wherein said organ is a gonadal organ.

22. The transgenic see-through medaka according to claim 14 wherein said organ is a gonadal organ.

23. A transgenic see-through medaka produced by repeated selective mating between iridophore deficient mutant medaka strain gu, albino mutant medaka strain i-3 and leucophore deficient mutant medaka strain lf, wherein a transgene being a fusion of a promoter of a gene which expresses specifically in a specific organ, with a coding region of a gene encoding a fluorescent protein, is introduced into the produced see-through medaka, and/or is carried by at least one of the iridophore deficient mutant medaka strain gu, albino mutant medaka strain i-3 and leucophore deficient mutant medaka strain lf, so that the transgenic see-through medaka has in its genome said transgene, and wherein said fluorescent protein is expressed specifically in said organ.

24. A transgenic see-through medaka produced by repeated selective mating between iridophore deficient mutant medaka strain gu, albino mutant medaka strain i-3, leucophore deficient mutant medaka strain lf and medaka FLF strain which is deficient in leucophores in the female, wherein a transgene being a fusion of a promoter of a gene which expresses specifically in a specific organ, with a coding region of a gene encoding a fluorescent protein, is introduced into the produced see-through medaka, and/or is carried by at least one of the iridophore deficient mutant medaka strain gu, albino mutant medaka strain i-3, leucophore deficient mutant medaka strain lf and medaka FLE strain which is deficient in leucophores in the female, so that the transgenic see-through medaka has in its genome said transgene, and wherein said fluorescent protein is expressed specifically in said organ.

25. The transgenic see-through medaka according to claim 23 wherein said gene encoding the fluorescent protein is a gene encoding a green fluorescent protein.

26. The transgenic see-through medaka according to claim 24 wherein said gene encoding the fluorescent protein is a gene encoding a green fluorescent protein.

27. The transgenic see-though medaka according to claim 23 wherein said organ is a gonadal organ.

28. The transgenic see-through medaka according to claim 24 wherein said organ is a gonadal organ.

29. The transgenic see-through medaka according to claim 25 wherein said organ is a gonadal organ.

30. The transgenic see-through medaka according to claim 26 wherein said organ is a gonadal organ.

* * * * *

UNITED STATES PATENT AND TRADEMARK OFFICE
CERTIFICATE OF CORRECTION

PATENT NO. : 6,737,559 B2
DATED : May 18, 2004
INVENTOR(S) : Yuko Wakamatsu et al.

It is certified that error appears in the above-identified patent and that said Letters Patent is hereby corrected as shown below:

<u>Title page,</u>
Item [75], Inventor, "Chikuda-ku," should read -- Chikusa-ku, --.

<u>Column 27,</u>
Line 21, "by means of repeated" should read -- by repeated --.
Line 47, "ELF" should read -- FLF --.

<u>Column 28,</u>
Line 20, "melanopores" should read -- melanophores --.

<u>Column 30,</u>
Line 9, "FLE" should read -- FLF --.
Line 21, "see-though" should read -- see-through --.

Signed and Sealed this

Twenty-eighth Day of June, 2005

JON W. DUDAS
*Director of the United States Patent and Trademark Office*